US005905166A

United States Patent [19]

Kiekens

[11] Patent Number: 5,905,166

[45] Date of Patent: May 18, 1999

[54] TYPE OF DYE IN PHOTOGRAPHIC MATERIALS

[75] Inventor: Eric Kiekens, Zele, Belgium

[73] Assignee: Agfa-Gevaert, N.V., Mortsel, Belgium

[21] Appl. No.: 08/909,723

[22] Filed: Aug. 12, 1997

Related U.S. Application Data

[62] Division of application No. 08/654,715, May 29, 1996, Pat. No. 5,688,636.

[30] Foreign Application Priority Data

Jun. 6, 1995 [EP] European Pat. Off. .............. 95201479

[51] Int. Cl.$^6$ .................................................. C07C 229/36

[52] U.S. Cl. .......................... 562/450; 548/493; 548/540; 549/488; 560/106; 560/19; 562/1; 562/433; 562/457; 562/464; 564/163

[58] Field of Search ............................................. 562/450

[56] References Cited

U.S. PATENT DOCUMENTS 5,298,652 3/1994 Carson et al. .......................... 562/444

OTHER PUBLICATIONS

Kiekens et al., CA 121:121613, 1994.
Haruki, CA 87:134654, 1977.

*Primary Examiner*—Laura L. Stockton
*Attorney, Agent, or Firm*—Breiner & Breiner

[57] ABSTRACT

A new type of yellow dyes with general formula Q-CO—CO—X is disclosed. They can be used in photographic materials as antihalation dyes, acutance dyes or filter dyes. Preferably they are incorporated in UV sensitive contact materials for pre-press applications.

1 Claim, No Drawings

TYPE OF DYE IN PHOTOGRAPHIC MATERIALS

This is a division of application Ser. No. 08/654,715 filed May 29, 1996, now U.S. Pat. No. 5,688,636.

FIELD OF THE INVENTION

The present invention concerns a photographic material containing a new type of dye.

BACKGROUND OF THE INVENTION

Light-absorbing dyes incorporated in silver halide photographic materials can accomplish a variety of goals, including their use as filter dyes, acutance dyes or anti-halation dyes.

When present in a non-photosensitive top layer or intermediate layer they typically serve as filter dyes eliminating an unwanted part of the light spectrum of the exposure source. A well-known example is the yellow filter layer usually present in colour photographic materials in order to prevent blue light from reaching the green sensitive and red sensitive layers. Another example is formed by UV-absorbing compounds, usually present in the top protective layer, which prevent photochemical deterioration of the image dyes formed by colour development. Examples of useful UV-absorbers include the cyanomethyl sulfone-derived merocyanines of U.S. Pat. No. 3,723,154, the thiazolidones, benzotriazoles and thiazolothiazoles of U.S. Pat. Nos. 2,739,888, 3,253,921, 3,250,617 and 2,739,971, the triazoles of U.S. Pat. No. 3,004,896, and the hemioxonols of U.S. Pat. No. 3,125,597.

On the other hand light-absorbing dyes when present in the emulsion layer can serve as so-called “acutance dyes” or “screening dyes” improving the image sharpness by reducing the sidewise scattering of light by the emulsion grains.

In a third application light-absorbing dyes act as “anti-halation dyes” improving the image sharpness by diminishing the upward reflection of light by the support into the emulsion layer. For this purpose the dye can be incorporated in an undercoat, being a non-photosensitive layer between the emulsion layer and the support, or it can be incorporated in the base itself, or preferably, it can be present in one or more backing layers of the photographic material.

Useful dyes absorbing in the visible spectral region include, for instance, the coloured pigments of U.S. Pat. No. 2,697,037, the pyrazolone oxonol dyes of U.S. Pat. No. 2,274,782, the styryl and butadienyl dyes of U.S. Pat. No. 3,423,207, the diaryl azo dyes of U.S. Pat. No. 2,956,879, the merocyanine dyes of U.S. Pat. No. 2,527,583, the merocyanine and oxonol dyes of U.S. Pat. Nos. 3,486,897, 3,652,284 and 3,718,472, and the enaminohemioxonol dyes of U.S. Pat. No. 3,976,661. Absorbing dyes can be added as particulate dispersions as disclosed in U.S. Pat. No. 4,092, 168, EP 0 274 723 and EP 0 299 435.

The dyes incorporated in one or more particular hydrophilic layers of a photographic material may be water-soluble. In this case they are easy diffusible to adjacent layers during coating and drying. For some particular applications, e.g. when serving as antihalation dyes in a sublayer or subcoat positioned between emulsion layer and support, the dyes are preferably non-diffisuble in order to retain a maximal concentration and density in said subcoat. By this is meant non-diffusible under normal coating conditons the pH of the coating solution being neutral or slightly acid depending on the isoelectric point of the gelatin used and the chemical nature of the dye. Under alkaline processing conditions the dye may become diffusable and/or may discolour. Non-diffusable dyes are described in e.g. GB 1.563.809, EP 0 015 601, and a survey can be found in Unexamined Japanese Patent Publications (Kokai) 03-24539, 03-4223, 02-9350, 02-282240 and 03-1133. New classes are recently disclosed in European Patent Publications No’s 0 582 753 and 0 587 229.

Light-absorbing dyes must fulfil a number of strict requirements. They should wash-out or decolourize as completely as possible during photographic processing in order to minimize unwanted residual dye stain. When washed-out they or their reaction products should not deteriorate the physical or sensitometric properties of the photographic material during prolonged continuous processing. Moreover, in order to be effective during exposure, the spectral characteristics of incorporated anti-halation dyes or acutance dyes should match as good as possible the spectral sensitivity distribution of the emulsion layer. In its turn this spectral sensitivity distribution has to be tuned to the spectral characteristic of the exposure source.

In pre-press graphic arts particular contact materials exist for quite some time which can be handled in UV poor roomlight. Such so-called Daylight or Roomlight materials are image-wise exposed by means of exposure sources, rich in near UV and short blue light, such as metal-halogen vapour lamps and quartz-halogen sources. Therfore dyes for use in such materials for filter-, acutance- or antihalation purposes must show an absorption spectrum comprised between about 300 to 450 nm with a wavelenght of maximal absorption situated about 350–380 nm.

Prior art on such dyes, which can be called with equal right UV-absorbers since they absorb partially in the near UV and partially in the blue spectral region, is disclosed in e.g. EP 0 252 550, U.S. Pat. Nos. 4,311,787, 4,082,554, 4,053,315, EP 0 519 306, EP 0 524 593, EP 0 524 594, EP 0 529 737, JP-A 03-38636, JP-A 03-13936, JP-A 03-41442, DE 4142935, EP 0 552 010, JP-A 03-48234, U.S. Pat. No. 5,155,015, EP 0 525 445, WO 93/5443, JP-A 03-78741, WO 93/13458, U.S. Pat. No. 4,923,788, EP 0 411 819, JP-A 61-205934, JP-A 01-259358, JP-A 02-73343, JP-A 02-71261 and EP 0 495 406.

It is an object of the present invention to provide a new class of yellow dyes for use in photographic materials and more particularly in graphic arts contact materials.

It is a further object of the present invention to provide a class of yellow dyes with high extinction in the near UV and short blue region and which show low residual stain after processing.

SUMMARY OF THE INVENTION

The objects of the present invention are realized by incorporating in a photographic material dyes represented by following general formula (I):

$$Q\text{-}CO—CO—X \qquad (I)$$

wherein Q represents a substituted or unsubstituted carbocyclic aromatic or hetero-aromatic ring, and -X represents $—N(R^1)(R^2)$ or $—OR^3$, wherein each of $R^1$, $R^2$ and $R^3$ independently represents H, substituted or unsubstituted alkyl or substituted or unsubstituted aryl, with the proviso that at least one of the R groups or a substituent of Q contains a water- or alkali-solubilising group.

In a preferred embodiment Q- represents Y-Ar- wherein wherein Ar represents a substituted or unsubstituted carbocyclic aromatic ring, and Y- represents —N($R^4$)($R^5$) or —O$R^6$, wherein $R^4$, $R^5$ and $R^6$ have the same definition as given for $R^1$, $R^2$ and $R^3$. In a most preferred embodiment Y- represents —N($R^4$)($R^5$).

DETAILED DESCRIPTION OF THE INVENTION

The present invention will now be explained in detail on the hand of its preferred embodiment wherin Q=Y-Ar and wherein Y=N($R^4$)($R^5$).

There are three general methods for the synthesis of this kind of compounds. we will explain them on the hand of the case wherein Y is a dimethylaniline residue:

Method A:

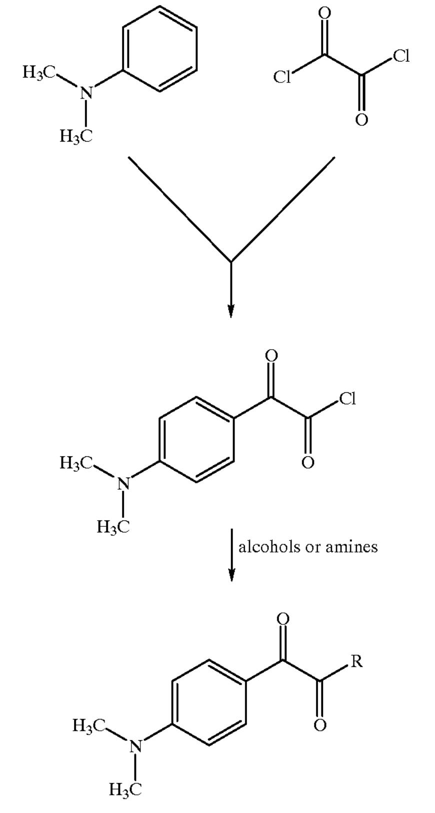

Method B:

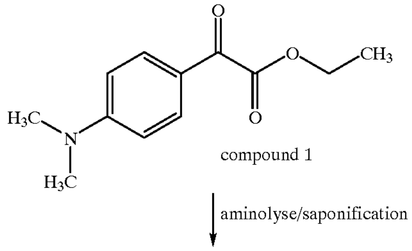

compound 1

-continued

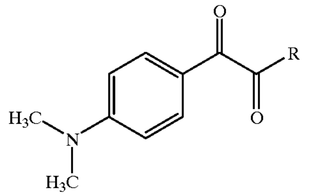

The synthesis of the starting compound of method B (Comp.-1) can be found in the following references:

H. Staudinger, H. Stockmann, *Chem. Ber.* 42, (1909), p. 3485,

M. Guyot, *Compt. Rend.,* 144, (1907), p.1120,

Michler, Hanhardt, *Berichte,* 10, (1877), p. 2081.

Method C:

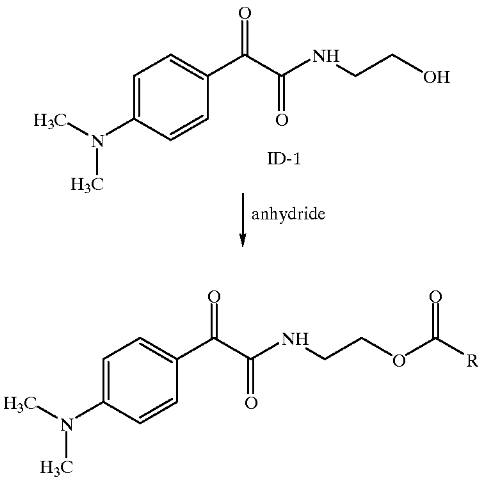

ID-1

The starting compound of method C is itself a dye according to the present invention (ID-1). I can be obtained itself according to method A or B. An example of its synthesis will be illustrated in preparative example 4.

Further useful dyes according to the present invention include:

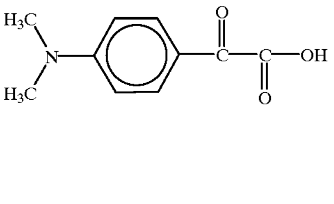

ID-2

-continued
ID-3
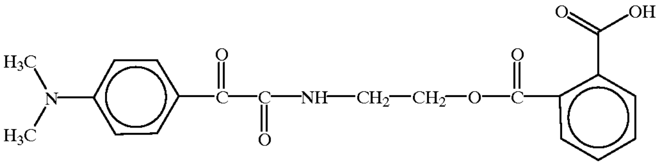
ID-4
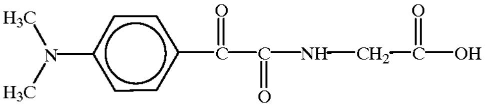
ID-5
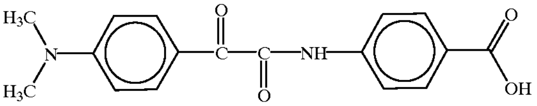
ID-6
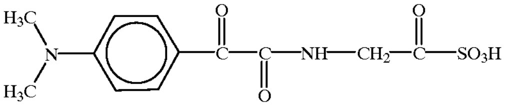
ID-7
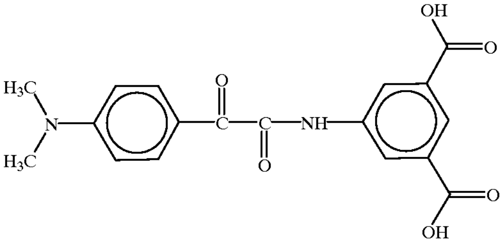
ID-8
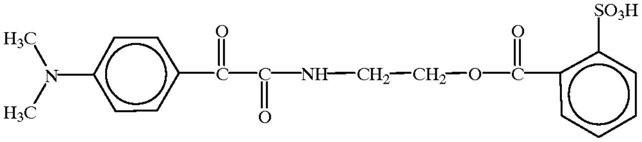
ID-9
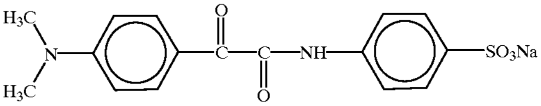
ID-10
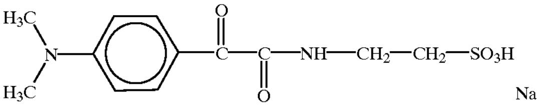
ID-11
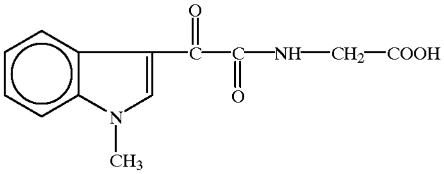

-continued

ID-12

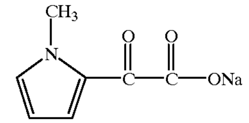

ID-13

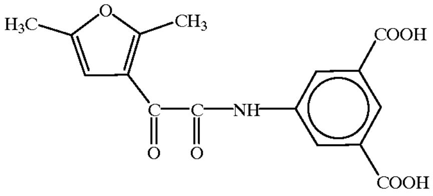

ID-14

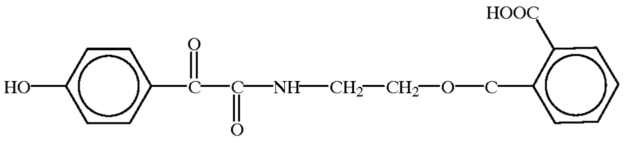

ID-15

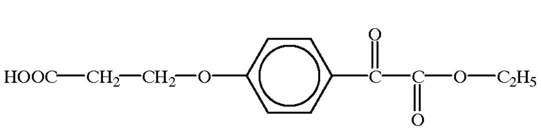

ID-16

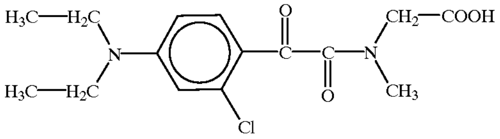

ID-17

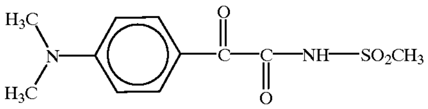

ID-18

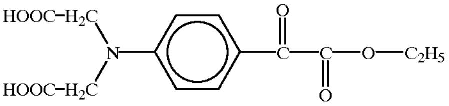

ID-19

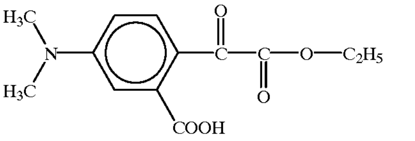

Dependent on their particular application the invention dyes are incorporated in the emulsion layer or in a non-light-sensitive layer. When serving as antihalation dyes they can be incorporated in a subcoat positioned between emulsion layer and support, or in a backing layer. When used as filter dyes they will be present in the protective top layer. Finally, when serving as acutance dyes they are incorporated in the emulsion layer itself. Preferably they are incorporated in such an amount per $m^2$ that an optical density (UV) ranging between 0.1 and 1.5 in that particular layer is obtained.

For most purposes the application of only one particular invention dye will be sufficient but, in principle, a mixture of two or more dyes can be applied.

The emulsion or mixture of emulsions of the photographic material in connection with the present invention can be incorporated in one single layer but, alternatively, a double emulsion layer or even a multiple layer pack can be applied.

The halide composition of the silver halide emulsions used in accordance with the present invention is not specifically limited and may be any composition selected from e.g. silver chloride, silver bromide, silver iodide, silver chlorobromide, silver bromoiodide, and silver chlorobromoiodide.

The photographic emulsion(s) can be prepared from soluble silver salts and soluble halides according to different methods as described e.g. by P. Glafkidès in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966). They can be prepared by mixing the halide and silver solutions in partially or fully controlled conditions of temperature, concentrations, sequence of addition, and rates of addition. The silver halide can be precipitated according to the single-jet method, the double-jet method, the conversion method or an alternation of these different methods.

The silver halide particles of the photographic emulsion (s) may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

The silver halide grains may have a multilayered grain structure. According to a simple embodiment the grains may comprise a core and a shell, which may have different halide compositions and/or may have undergone different modifications such as the addition of dopes. Besides having a differently composed core and shell the silver halide grains may also comprise different phases inbetween.

Two or more types of silver halide emulsions that have been prepared differently can be mixed for forming a photographic emulsion for use in accordance with the present invention.

The average size of the silver halide grains may range from 0.05 to 1.0 micron, preferably from 0.2 to 0.5 micron. The size distribution of the silver halide particles can be homodisperse or heterodisperse.

The silver halide crystals can be doped with $Rh^{3+}$, $Ir^{4+}$, $Cd^{2+}$, $Zn^{2+}$ or $Pb^{2+}$.

The emulsion can be desalted in the usual ways e.g. by dialysis, by flocculation and re-dispersing, or by ultrafiltration.

The light-sensitive silver halide emulsions are preferably chemically sensitized as described e.g. in the above-mentioned "Chimie et Physique Photographique" by P. Glafkidès, in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners or by means of reductors e.g. tin compounds as described in GB 789,823, amines, hydrazine derivatives, formamidine-sulphinic acids, and silane compounds. Chemical sensitization can also be performed with small amounts of Ir, Rh, Ru, Pb, Cd, Hg, Tl, Pd, Pt, or Au. One of these chemical sensitization methods or a combination thereof can be used.

The silver halide emulsion(s) for use in accordance with the present invention may comprise compounds preventing the formation of fog or stabilizing the photographic characteristics during the production or storage of photographic elements or during the photographic treatment thereof. Many known compounds can be added as fog-inhibiting agent or stabilizer to the silver halide emulsion. Suitable examples are e.g. the heterocyclic nitrogen-containing compounds such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB 1,203,757, GB 1,209,146, JA-Appl. 75-39537, and GB 1,500,278, and 7-hydroxy-s-triazolo-[1,5-a]-pyrimidines as described in U.S. Pat. No. 4,727,017, and other compounds such as benzenethiosulphonic acid, benzenethiosulphinic acid and benzenethiosulphonic acid amide. Other compounds that can be used as fog-inhibiting compounds are metal salts such as e.g. mercury or cadmium salts and the compounds described in Research Disclosure N° 17643 (1978), Chapter VI.

The fog-inhibiting agents or stabilizers can be added to the silver halide emulsion prior to, during, or after the ripening thereof and mixtures of two or more of these compounds can be used.

Besides the silver halide another essential component of a light-sensitive emulsion layer is the binder. The binder is a hydrophilic colloid, preferably gelatin. Gelatin can, however, be replaced in part or integrallly by synthetic, semi-synthetic, or natural polymers. Synthetic substitutes for gelatin are e.g. polyvinyl alcohol, poly-N-vinyl pyrrolidone, polyvinyl imidazole, polyvinyl pyrazole, polyacrylamide, polyacrylic acid, and derivatives thereof, in particular copolymers thereof. Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting of polymerizable monomers on gelatin, and cellulose derivatives such as hydroxyalkyl cellulose, carboxymethyl cellulose, phthaloyl cellulose, and cellulose sulphates.

The binders of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

As already mentioned, beside the light-sensitive emulsion layer(s) the photographic material can contain several non-light-sensitive layers, e.g. a protective top layer, one or more backing layers, and one or more intermediate or subcoat layers.

The photographic material of the present invention may further comprise various kinds of surface-active agents in the photographic emulsion layer or in another hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Such surface-active agents can be used for various purposes e.g. as coating aids, as compounds preventing electric charges, as compounds improving slidability, as compounds facilitating dispersive emulsification, as compounds preventing or reducing adhesion, and as compounds improving the photographic characteristics e.g higher contrast, sensitization, and development acceleration. Preferred surface-active coating agents are compounds containing perfluorinated alkyl groups.

Apart from the light-absorbing dye(s) and the sensitizing dye(s) a so-called "recognition dye" can be present, preferably in a backing layer. Such a dye exerts no photographic activity but enhances the visual difference under faint dark room illumination between the emulsion layer side and the backing layer side.

The photographic elements in connection with the present invention may further comprise various other additives such as e.g. compounds improving the dimensional stability of the photographic element, spacing agents and plasticizers.

Suitable additives for improving the dimensional stability of the photographic elements are e.g. dispersions of a water-soluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, Alpha-Beta-unsaturated dicarboxylic acids, hydroxyalkyl (meth) acrylates, sulphoalkyl (meth)acrylates, and styrene sulphonic acids.

Spacing agents can be present, preferably in the top protective layer; in general the average particle size of such spacing agents is comprised between 0.2 and 10 micron. They can be soluble or insoluble in alkali. Alkali-insoluble spacing agents usually remain permanently in the photographic element, whereas alkali-soluble spacing agents usually are removed therefrom in an alkaline processing bath. Suitable spacing agents can be made e.g. of polymethyl methacrylate, of copolymers of acrylic acid and methyl methacrylate, and of hydroxypropylmethyl cellulose hexahydrophthalate. Other suitable spacing agents have been described in U.S. Pat. No. 4,614,708.

The support of the photographic materials in connection with the present invention can be transparent base, preferably an organic resin support, e.g. cellulose nitrate film, cellulose acetate film, polyvinylacetal film, polystyrene film, polyethylene terephthalate film, polycarbonate film, polyvinylchloride film or poly-Alpha-olefin films such as polyethylene or polypropylene film. The thickness of such organic resin film is preferably comprised between 0.07 and 0.35 mm. These organic resin supports are preferably coated with a subbing layer. On the other hand the support of the photographic material can be a paper base preferably a polyethylene or polypropylene coated paper base.

The use of the photographic material of the present invention is not limited to any particular field. However in a preferred embodiment the photographic material is a UV sensitive contact material (roomlight material) for pre-press graphic arts.

The photographic materials according to the invention can be processed by any means or any chemicals known in the art depending on their particular application. In the case of UV sensitive elements in the field of contacting they are preferably processed in so-called "Rapid Access" chemicals, comprising a conventional Phenidone/hydroquinone developing solution and a conventional sodium or ammonium thiosulphate containing fixing solution. The development time is usually between 10 and 30 seconds at a temperature of about 35° C. Alternatively they can be processed in so-called "hard dot Rapid Access" chemistry, e.g. the AGFASTAR system marketed by Agfa-Gevaert N.V.. Preferably an automatically operated processor provided with automatic regeneration is used, e.g. a RAPILINE device marketed by Agfa-Gevaert N.V..

The present invention is illustrated by the following examples without however being limited thereto.

EXAMPLES

A. Preparative Examples

Apart from Comp. 1 and dye ID-1 the following starting compounds are used in the following preparative examples:

Comp. 2

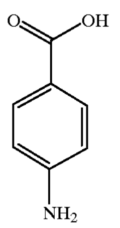

Comp. 3

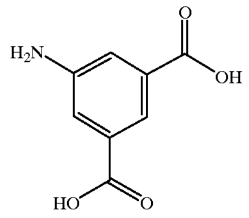

Comp. 4

$H_2N—CH_2—CH_2—SO_3H$

Example 1

Preparation of ID-5 According to Method A 512 ml of dimethylaniline were allowed to react with 176 ml of oxalylchloride for 24 h in 800 ml of butylacetate at 0° C. in order to avoid elimination of CO. The reaction mixture was diluted with 700 ml of dimethylacetamide in order to obtain complete dissolution. Then ⅓ of this reaction mixture A was added dropwise to a solution of 25 g of Comp. 2 in 250 ml of dimethylacetamide. After acidification with 500 ml of HCl 2N the precipitate formed was filtrated, digested in 250 ml of ethanol/water (4:1) and in 100 ml of acetic acid. Finally the precipitate, a green-yellow powder, was washed with acetone. The yield was 38%.

Example 2

Preparation of ID-7 According to Method A

⅓ of the reaction mixture A mentioned above was added to a solution of 25 g of Comp.3 in 250 ml of dimethylacetamide. After acidification with 500 ml of HCl 2N the precipitate formed, an ochre-yellow powder, was filtered off and washed with 1 l of methanol. The yield was 86%.

Example 3

Preparation of ID-2 According to Method B 150.3 g of Comp. 1 were dissolved in 1500 ml of NaOH 1N en precipitated again by means of 1 l of HCl 1.8N. The obtained precipitate, an ochre-yellow powder was filtered off and washed with 500 ml of water. The yield was 86%.

Example 4

Preparation of ID-1 According to Method B 110.5 g of Comp. 1 were dissolved in 500 ml of ethylacetate/methylene chloride (1:1) and were stirred with ethanolamine. The formed precipitate, a yellow powder, was filtered off and washed with 200 ml of acetone. The yield was 71%.

Example 5

Preparation of ID-4 According to Method B 22.1 g of Comp. 1 and 75.1 g of glycine were refluxed in the presence of 198 g of 30% sodium methylate in methanol. The formed precipitate (Na salt) was filtered off and washed with 1 l of acetone. By acidification with 700 ml of acetic acid the free acid, a lightly yellow powder, was obtained. Yield: 40%.

Example 6

Preparation of ID-10 According to Method B

A solution of 22.1 g of Comp.1 was refluxed together with 12.5 g of Comp.4 and 18.8 g of 30% sodium methylate in 200 ml of methanol. The precipitate formed, a lightly yellow powder, was filtered off. The yield was 40%.

Example 7

Preparation of ID-3 According to Method C 23.6 g of ID-1 was heated with 60 g of benzoic anhydride in toluene and an equivalent amount of pyridine (8.85 ml) for 5 days. The reaction mixture was reduced by evaporation and treated with 300 ml of a mixture of HCl 1.6N/methylenechloride (1:1). The organic fraction was reduced by evaporation and purified by means of preparative column chromatography with methylenechloride/ethyl acetate (97:3) as eluent. The compound obtained was a yellow powder. The yield was 25%.

Example 8

Preparation of ID-8 According to Method C 23.6 g of ID-1 were refluxed together with 20.2 g of sulphobenzoic anhydride and 9 ml of pyridine in 200 ml of toluene. The oil formed was taken up in 300 ml of NaOH 1N and again heated to reflux with 200 ml of toluene. After elimination of the solvents by evaporation the precipitate formed was taken up in 500 ml of methanol. The precipitate, a lightly yellow powder, dissolved but recrystallized immediately. The yield was 54%.

B. Photographic Examples

Example 9

A control element A was prepared comprising a poly (ethylene terephthalate) film support, a silver halide emulsion layer overlying the film support, and a protective overcoat layer overlying the silver halide emulsion layer. The silver halide emulsion layer contained a silver chloride emulsion having an average grain size of 0.08 μm which was doped with 60 ppm Rhodium and which was gold sensitized. Other ingredients of the emulsion were 0.008 mole of 4-hydroxy-6-methyl-(1,3,3a,7)-tetraazaindene per mole of silver halide and 0.008 mole of 5-nitroindazole per mole of silver halide. The emulsion layer also contained a poly-[ethylacrylate-co-sodium-4-(11-(methacryloylamino)-undecanoylamino)benzene sulfonate] in an amount of one part per part by weight of the hydrophilic colloid.

The emulsion was coated at a silver coverage of 3.8 g/m$^2$ and at a gelatin coverage of 1.7 g/m$^2$.

The protective overcoat layer contained gelatin, the hardening agent formaldehyde, and poly(methylmethacrylate) beads at a concentration of 0.63 parts per part of gelatin. The overcoat layer was coated at a gelatin coverage of 0.7 g/m$^2$.

Invention elements B, C, D and E were identical to element A with the exception that the overcoat layer contained dye ID-2, ID-4, ID-5 and ID-10 respectively in an amount as indicated in table 1. At the opposite side of the support an antihalation layer was coated containing contol dye CD-1 at a coverage of 0.01 g/m$^2$. This control dye CD-1 had following formula:

CD-1

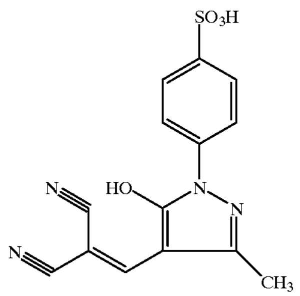

The elements were exposed to a halftone test pattern including a 50% dot area by means of an overexposure of six times the normal exposure needed to produce a negative having a 50% dot area.

The elements were processed in an Agfa graphic processor RAPILINE 66A containing a conventional hydroquinone-Phenidone developer and a conventional fixing solution containing ammonium thiosulphate at a temperature of 35° C. After processing, the dot shift due to the overexposure, compared to the orignal 50% dot, was measured and the staining was evaluated.

The results in table 1 show that the new dyes are very suitable as filter dyes in order to enhance the exposure latitude of a contact film.

TABLE 1

| Element | Dye | g/m$^2$ | Sensitivity$^{(1)}$ | Dot shift | Staining |
|---|---|---|---|---|---|
| A | — | 0 | 50 | 8% | OK |
| B | ID-2 | 0.1 | 108 | 5% | OK |
| C | ID-4 | 0.1 | 96 | 3% | OK |
| D | ID-5 | 0.1 | 97 | 4% | OK |
| E | ID-10 | 0.1 | 99 | 4% | OK |

$^{(1)}$Sensitivity: expressed as relative log H in order to get a density of 3.0. A higher figure means lower sensitivity.

Example 10

Elements F and G were identical to element A with the exception that an antihalation layer was positioned between the emulsion layer and the support instead of at the opposite side. This antihalation layer contained gelatin at a coverage of 1 $g/m^2$ and polyethylacrylate latex at a coverage of 1 $g/m^2$. Control element F served as comparison and contained no dye, while invention element G contained dye K. The elements F and G were evaluated in the same manner as the elements A, B, C, D and E. The results are presented in table 2.

TABLE 2

| Element | Dye | $g/m^2$ | Sensitivity | Dot shift | Staining |
|---|---|---|---|---|---|
| F | — | 0 | 50 | >10% | OK |
| G | ID-4 | 0.1 | 102 | 2% | OK |

As indicated in table 2, the benefits of the present invention become even more pronounced in a material design wherein the antihalation layer is not present at the opposite side but is positioned between the emulsion layer and the support.

I claim:

1. A dye represented by the formula

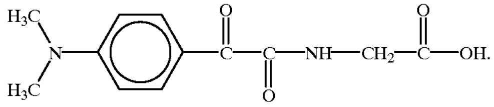

* * * * *